United States Patent [19]

Vanzetti et al.

[11] Patent Number: 4,481,418
[45] Date of Patent: Nov. 6, 1984

[54] FIBER OPTIC SCANNING SYSTEM FOR LASER/THERMAL INSPECTION

[75] Inventors: Riccardo Vanzetti, Brockton; Ashod S. Dostoomian, Stoughton; Alan C. Traub, Framingham, all of Mass.

[73] Assignee: Vanzetti Systems, Inc., Stoughton, Mass.

[21] Appl. No.: 429,397

[22] Filed: Sep. 30, 1982

[51] Int. Cl.³ .............................................. G01J 1/00
[52] U.S. Cl. .................................. 250/338; 250/341; 250/347
[58] Field of Search ............ 250/341, 347, 338, 358.1, 250/461.1; 356/44

[56] References Cited

U.S. PATENT DOCUMENTS

| | | | |
|---|---|---|---|
| 3,803,413 | 4/1974 | Vanzetti et al. | 250/338 |
| 4,127,773 | 11/1978 | West | 250/461.1 |
| 4,214,164 | 7/1980 | Traub et al. | 250/358.1 |
| 4,376,890 | 3/1983 | Engström et al. | 250/461.1 |

*Primary Examiner*—Janice A. Howell
*Attorney, Agent, or Firm*—Sughrue, Mion, Zinn, Macpeak and Seas

[57] ABSTRACT

An apparatus for inspecting a device made up of a plurality of different infrared radiating elements includes an optical head which is moveable along X-Y coordinates above the fixed device to sequentially scan the infrared radiating elements. A laser beam source is operatively connected to the moveable head for injecting thermal energy into the infrared radiating elements and an infrared detector is provided for sensing the infrared radiation emanating from the elements. The infrared detector may be mounted directly on the moveable head or in a remote location wherein the detector would be connected to the moveable head by a flexible optical fiber. A second moveable head may be located on the opposite side of the device so that thermal energy from the laser source may be injected into opposite sides of the infrared radiating element.

5 Claims, 3 Drawing Figures

FIBER OPTIC SCANNING SYSTEM FOR LASER/THERMAL INSPECTION

BACKGROUND OF THE INVENTION

The present invention is directed to an inspection system wherein a component is heated by means of a laser beam to produce thermal radiation which is measured by an infrared detection system to produce an output indicative of the component characteristics and more specifically to a fiber optic system for transmitting the laser beam and the infrared radiation to and from a scanning head movable along X-Y coordinates.

The general principles of the laser beam-infrared detector inspection system are disclosed in the Vanzetti et al U.S. Pat. No. 3,803,413, granted Apr. 9, 1974. This patent discloses the concept of using a positioning table upon which an electronic circuit board assembly is positioned so that its components may be tested in sequence. As each component (in this instance a solder joint) is brought into the testing position, it is subjected to a laser beam heat injection pulse during and after which its heating and cooling history, as monitored by an infrared detection system, reveals information about its quality. In this patent, the table upon which the printed circuit board is supported is moved along one coordinate while a rotatable mirror deflects a laser beam in a scanning movement along another coordinate at right angles thereto. Upon further rotation of the mirror, the infrared radiation emitted by the heated solder joint is reflected to a suitable infrared detection system.

SUMMARY OF THE INVENTION

The present invention provides a new and improved inspection system wherein the object to be inspected is located in a fixed position and optical fibers are connected between a laser and an infrared detector at one end and a scanning head at the other end for movement along X-Y coordinates. In another embodiment, the infrared detector can be mounted directly on the scanning head for movement therewith. In still another embodiment, the scanning head connected by an optical fiber to a laser is located on one side of the object to be examined and an infrared detector is located on the opposite side of the object to be inspected. In this embodiment, the infrared detector may be mounted for movement along corresponding X-Y coordinates or may be stationary and connected to a scanning head by means of an optical fiber. It is contemplated that an arc lamp may be substituted for the laser and in each embodiment the infrared detector provides an output signal which may be compared with a previously stored signal indicative of an acceptable component.

The foregoing and other objects, features and advantages of the invention will be apparent from the following more particular description of preferred embodiments of the invention as illustrated in the accompanying drawings.

DETAILED DESCRIPTION OF THE INVENTION

Figure 1:
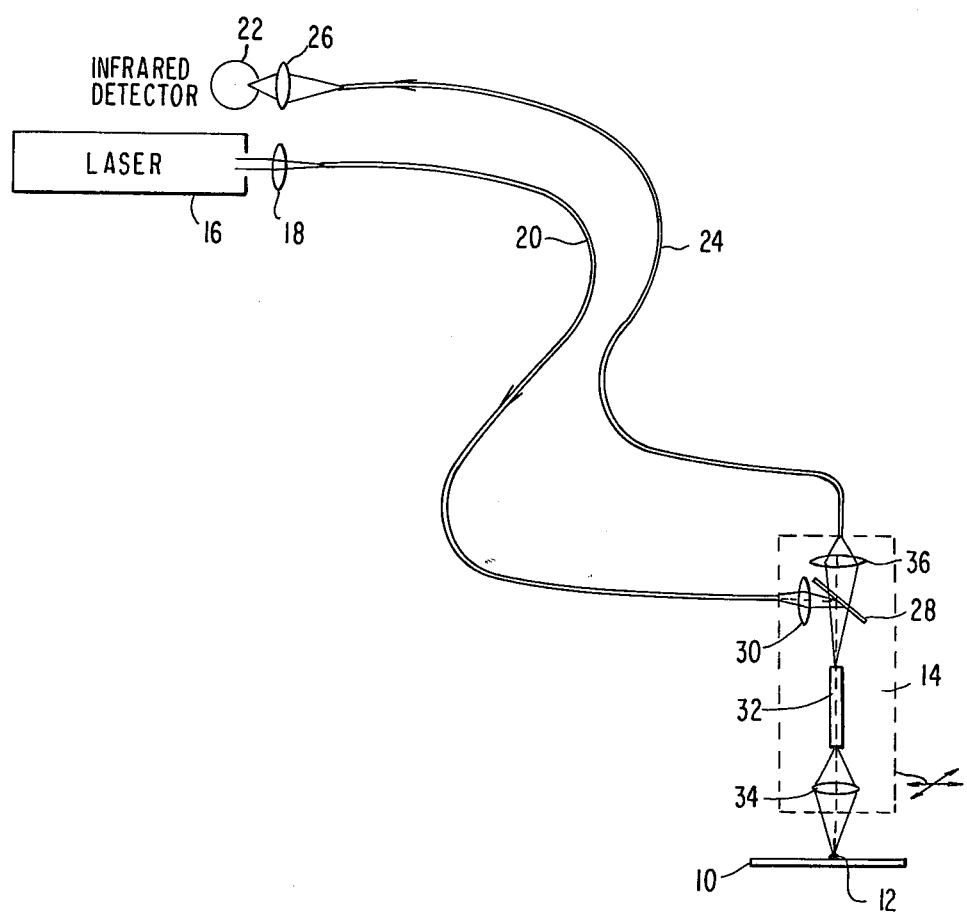
FIG. 1 is a schematic view of an inspection system according to a first embodiment of the present invention.

According to the first embodiment of the present invention, as illustrated in FIG. 1, a printed circuit board 10 having a plurality of solder joints, one of which is shown at 12, is positioned in a fixed location and an optical head 14 is moved along X-Y coordinates in a conventional manner to sequentially scan the solder joints 12 on the printed circuit board 10. A laser pulse is generated by a suitable laser device 16 which is directed through a lens 18 into a flexible optical fiber 20 which transmits the laser pulse to the optical head 14. A thermal-infrared detector 22 is also positioned in a stationary manner in the machine along with the laser 16 and receives thermal-infrared radiation from the solder joint 12 through a flexible optical fiber 24 and a lens 26. Although the ends of the optical fibers 20 and 24 carried by the movable head 14 may be disposed in close, side-by-side proximity for directing and receiving radiation respective to and from a solder joint 12 or may be optically imaged upon the same solder joint by separate optical systems, it is preferred to combine the optical paths of the separate fibers 20 and 24 into a single optical path for a short distance near the target end so that both the heating and detection functions may be associated with the target or solder joint over a single path. In the embodiment shown in FIG. 1 a dichroic beam splitter 28 is provided on the optical head 14 which serves as a clear window for one band of wave lengths and is a mirror for another selected band. The laser pulse transmitted by the optical fiber 20 is directed thru a lens 30 onto the dichroic mirror 28 and reflected into one end of a radiation transmitting member 32. The laser pulse emitted from the opposite end of the radiation transmitting device 32 is then focused on the solder joint 12 by means of a suitable lens system 34. The heated solder joint 12 produces thermal infrared radiation which is then transmitted back thru the lens system 34, the radiation transmitting member 32, the dichroic mirror 28 and a lens 36 for transmission to the thermal-infrared detector 22 by means of the optical fiber 24. The short common path defined by the radiation transmitting device 32 may be comprised of a sapphire rod or other material which transmits both wave bands or may be in the form of a hollow metallic tube capable of all-wave multiple internal reflection. The optical device 24 for reimaging the end face of the device upon the target may be an achromatic infrared lens or a reflective optical system. In lieu of separate, relatively heavy optical fibers 20 and 24 used in each branch a plurality of smaller diameter fibers whose target ends have been braided together in interspersed fashion may be used and appropriately separated at opposite ends for their respective purposes.

If a Nd:YAG or similar laser is chosen as the heating laser 16, the laser fiber 20 must be an effective transmitter in the 1-micrometer wavelength region. The detector fiber 24 is preferably a good transmitter in the 4-6 micrometer region in order to be able to accommodate the thermal radiation from the heated target. Correspondingly, the detector 22 should be chosen to be sensitive in this wave length region, a requirement which is satisfied by state of the art detectors such as cryogenically cooled indium antimonide, mercury-cadmium-telluride, and others which are known in the optical art.

The optical head 14 may be moved along the X-Y coordinates by any suitable means such as the means which would move the stylus on an X-Y chart recorder. By moving the optical head 14 a reduction in the enclosure size for the system can be achieved and because of the low mechanical inertia of the elements to be scanned, compared with the conventional positioning table, higher scanning rates can be achieved where intermittent motion is used because of the acceleration and deceleration times which would be relatively shorter than for most positioning tables. In the prior art method where the table supporting a printed circuit board is indexed along X-Y coordinates and the optical paths are fixed, a mechanical design constraint is imposed upon the system. If the system is to accommodate a board whose dimensions are A and B, then a table with a corresponding motion capability is obviously in order. However, in order to provide for corner-to-corner motion on the table, the enclosure about the table must be at least the dimensions 2A×2B. However, if it is merely the target ends of two flexible optical fibers which must be moved, as shown in FIG. 1, this may be done within an enclosure of dimensions A×B plus a small added amount to account for the modest dimension of the mechanical structure which secures the moving ends of the fibers plus any associated optics. Moderate additional clearance will be needed for the frame and other associated parts which cause the end fibers to traverse in orthogonal directions.

Optical fibers are known in the art which are capable of transmitting with great effectiveness concentrated beams of visible light or near-infrared laser-beam power of high power densities. An example of such an optical fiber is a 0.024 inch diameter high-purity fused silica fiber which can accept at least 30 watts of Nd:YAG laser power and can transmit it with a modest loss due to end-reflections and to internal absorption. For the thermally transmitting fiber a material is required with a longer-wavelength capability than is shown by fused silica. In recent years, several types of infrared-transmitting optical fibers have been under development using such materials as arsenic trisulphide, potassium chloride, tellurium oxide, zirconium fluoride, thallium-bromo-iodide and others. Thus, for the purposes of the present invention, a fused silica or other near-infrared transmitting fiber for use with a visible-band or near-IR heating laser and a fiber of one of the newer materials for transmitting the thermal infrared radiation to a suitable detector may be used. Alternatively, both fibers can be fashioned of the newer material and a heating laser may be of carbon dioxide, radiation at 10.6 micrometers.

Figure 2:
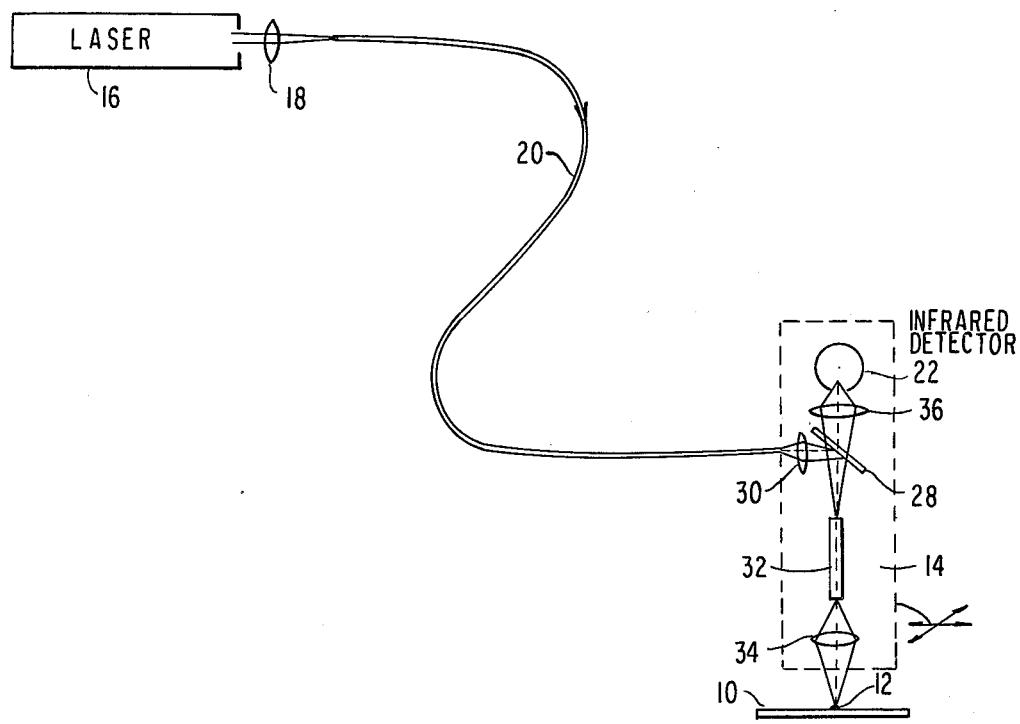
FIG. 2 is a schematic view of an inspection system according to a second embodiment of the present invention.

In the embodiment of FIG. 2, the arrangement of the laser, its associated optical fiber 20 and optical head 14, which moves relative to the target along X-Y coordinates, is identical to that shown in FIG. 1. The only difference resides in the fact that the thermal-infrared detector 22 has been mounted directly on the optical head 14 thereby eliminating the need for the lens 26 and the optical fiber 24. By utilizing such an arrangement it is possible to reduce the size of the detector-optical portion of the system in order that it may be placed more closely to the target area.

Figure 3:
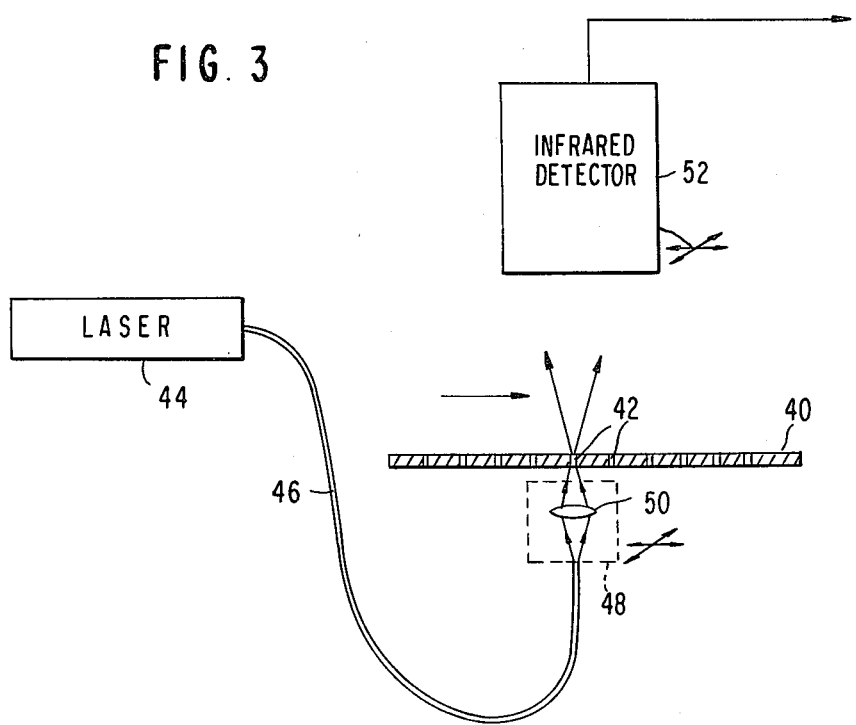
FIG. 3 is a schematic view of an inspection system according to a third embodiment of the present invention.

The arrangement shown in the embodiment of FIG. 3 is designed for use with a circuit board 40 having soldering masses 42 which extend through the board from one face to the other. The laser device 44 supplies a pulsed laser beam through an optical fiber 46 to a moveable head 48 having a suitable lens system 50 mounted thereon for focusing the laser beam on the solder mass or target 42. The thermal-infrared radiation emitted from the solder mass 42 on the opposite side of the circuit board is detected by a suitable detector system 52 which may be similar to the detector systems illustrated in FIGS. 1 and 2 with the moveable head. The moveable head 48 for the laser beam would be moved synchronously with the moveable head of the detector system 52 by conventional scanning mechanisms (not shown). Thus, the solder mass or joint 42 may be heated from the bottom and detected from the top so that variations in total solder mass may be more readily detectable. Such variations may be due to insufficient solder or to internal voids. Alternatively, this feature may be simply added to the existing design as is shown in FIGS. 1 and 2 so that the user has alternative options of heating each joint either from above or below. Either separate laser sources may be used for rapid and convenient switching of the two heating methods or a single laser may be used with its beam power being diverted alternately into two separate optical fibers. Beam diversion may be accomplished manually, such as by detecting one fiber input end from the laser and by substituting the other, or may be accomplished automatically.

The laser may be operated and the detector signal may be processed in the manner disclosed in the Vanzetti et al U.S. Pat. No. 3,803,413. It is also possible under limited conditions to use a high intensity arc lamp in lieu of a laser.

While the invention has been particularly shown in reference to preferred embodiments thereof, it will be understood by those in the art that the foregoing and other changes in form and details may be made therein without departing from the spirit and scope of the invention. For instance the target (a printed-circuit board) can be mounted on an X-Y positioning table, while the scanning head remains stationary.

What is claimed is:

1. An apparatus for inspecting a device made up of a plurality of different infrared radiating elements comprising means for mounting said device in a fixed position, moveable head means adapted to be moved along orthogonal axes in close proximity to said device, laser beam means, optical fiber means connecting said laser beam means with said moveable head means for injecting thermal energy into said device and detection means operatively associated with said moveable head means for detecting infrared radiation emanating from said device.

2. An apparatus as set forth in claim 1 wherein said detector means are fixed and optical fiber means are connected between said moveable head means and said detector means for transmitting infrared radiation to said detector means from said device.

3. An apparatus as set forth in claim 1 wherein said detector means is mounted on said moveable head means for detecting radiation emanating from said device.

4. An apparatus as set forth in claim 1, wherein said moveable head means is comprised of a first moveable head and a second moveable head disposed on opposite sides of said device for synchronous movement relative to said device, optical fiber means connecting said laser beam means to said first moveable head for injecting thermal energy into said device from one side and said detector means being operatively associated with said second moveable head for detecting infrared radiation emanating from the opposite side of said device.

5. An apparatus for inspecting a device made up of a plurality of different infrared radiation elements comprising moveable support means for supporting said device for movements along orthogonal axes, a fixed head mounted in closely spaced relation to said support means while providing clearance for said device, laser beam means, optical fiber means connecting said laser beam means with said head for injecting thermal energy into said device and detecting means mounted on said head for detecting radiation emanating from said device.

* * * * *